United States Patent [19]

Altner

[11] Patent Number: 4,802,667
[45] Date of Patent: Feb. 7, 1989

[54] WEIGHTLIFTER'S BELT

[76] Inventor: David J. Altner, 2415 Ridge Rd., Perkasie, Pa. 18944

[21] Appl. No.: 153,314

[22] Filed: Feb. 8, 1988

[51] Int. Cl.⁴ ............................................. A63B 13/00
[52] U.S. Cl. ....................................... 272/123; 2/338; 128/78
[58] Field of Search .................... 272/123, 143; 2/321, 2/322, 336, 338; 128/69, 75, 78, 87, 95.1, 133, 134

[56] References Cited

U.S. PATENT DOCUMENTS

| 4,135,503 | 1/1979 | Romano | 128/78 |
| 4,348,774 | 9/1982 | Woodson | 2/338 |
| 4,545,370 | 10/1985 | Welsh | 2/321 X |
| 4,622,957 | 11/1986 | Curlee | 128/78 |
| 4,685,668 | 8/1987 | Newlin, Jr. | 272/123 |
| 4,689,883 | 9/1987 | Daniels | 2/322 |
| 4,726,077 | 2/1988 | Batiste | 2/321 |

FOREIGN PATENT DOCUMENTS 3531573  3/1987  Fed. Rep. of Germany ...... 272/123

Primary Examiner—Richard J. Apley
Assistant Examiner—Robert W. Bahr
Attorney, Agent, or Firm—Joseph W. Molasky & Assocs.

[57] ABSTRACT

A belt that allows for various support levels to be applied to contiguous areas of a weightlifter's lower back and abdomen during an exercise program to prevent stress upon spinal discs and adjoining vertebrae. Support is provided to the abdomen and lower back through use of two independently functioning belt arrangements which allow staggered tightening with respect to one another and provide primary tension to the areas being supported. The belt may be adapted for heavy or alternatively light exercise moves.

5 Claims, 1 Drawing Sheet

U.S. Patent  Feb. 7, 1989  4,802,667
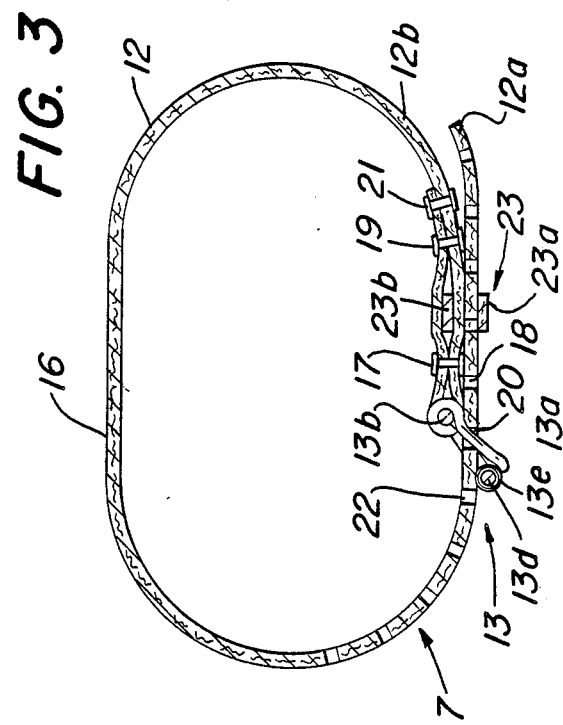
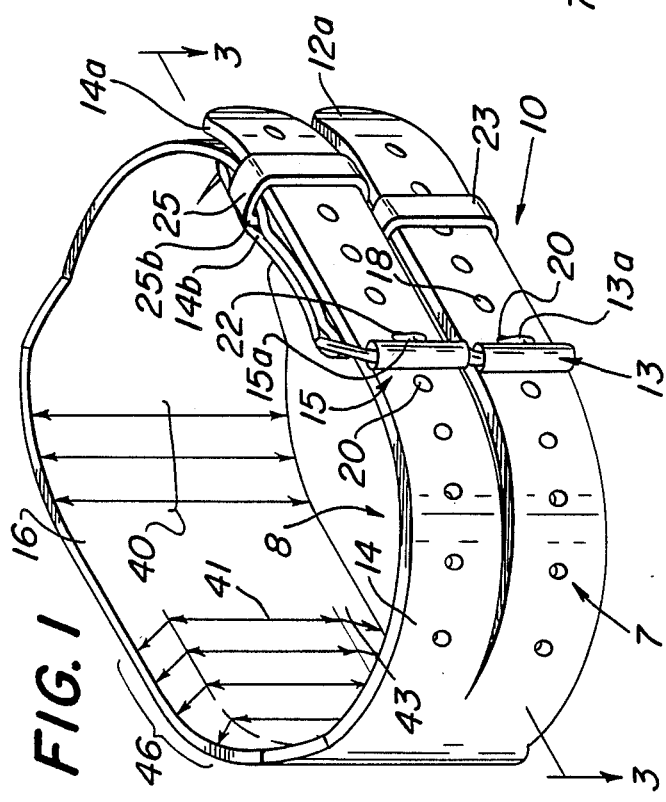
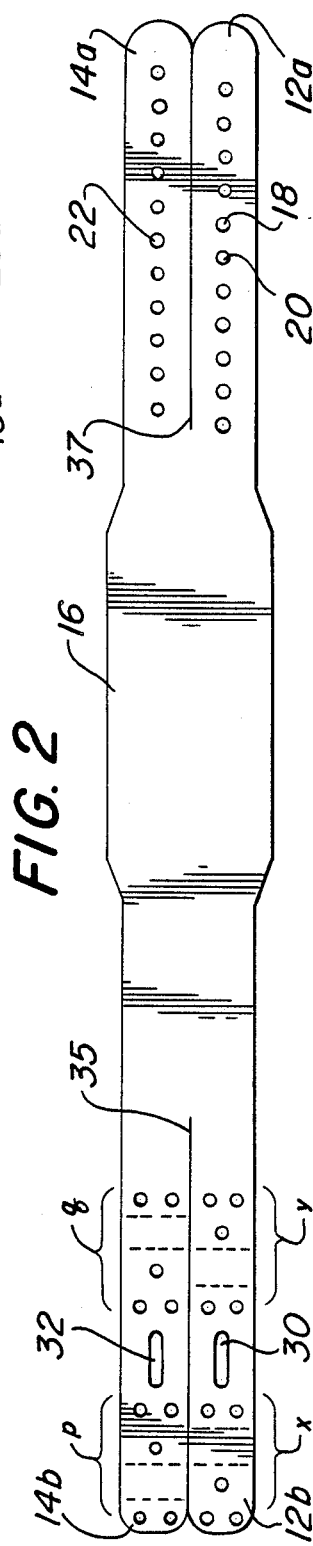

WEIGHTLIFTER'S BELT

BACKGROUND OF THE INVENTION

1. Field of the Invention

The invention relates to the field of weightlifting and in particular relates to a device for preventing injury due to induced stress upon the lower back area of a weightlifter.

2. Description of the Prior Art

It has been the prior practice of weightlifters to employ a single belt configuration when performing a heavy weightlifting exercise in order to prevent exaggerated arching of the back. However, it has been found that the single exercise belt arrangement is not satisfactory due to its failure to provide primary or full tension across the weightlifter's lower back and abdominal areas when heavy squats or overhead presses are being performed. This prior art shortcoming is deemed to be serious particularly when the exercise being conducted might place the spinal column in an endangered position. In addition, the prior art single belt configuration does not accommodate itself to varying torso dimensions of the weightlifter in the waist, and as a consequence, it is uncomfortable to wear when the various heavy exercises are being executed.

Another existing shortcoming of the prior art single belt arrangement is that it lacks versatility since it cannot be readily adapted when switching from heavy to light weightlifting moves. It is understood that when light exercises are being performed full tension is not required to be applied to the lower back area as in the case with heavy lifting.

It is also recognized that the prior art single weightlifter's support belt is deficient due to its propensity to stretch over long usage. Such stretching diminishes the amount of support supplied to the requisite muscle and skeletal areas and is obviously not beneficial to the user.

The lack of versatility, the inability to adjust to the varying dimensions of the weightlifter's waist area, the failure to apply a wide area of tension along the delicate back area and the tendency to stretch over time are prior art problems which are solved by the present invention.

BRIEF SUMMARY OF THE INVENTION

The instant invention is directed to a weightlifter's training belt for use when conducting light or heavy moves during an exercise program. The training belt of the present invention is comprised of dual component belts that fit around the abdominal area and which are integrally connected with a main lower back support member. The dual belt members are of equal length and utilize a plurality of staggered holes with respect to one another for buckling purposes to allow selective adjustment in accordance with varying circumferential dimensions of the weightlifter's waist. The staggered buckling arrangement allows equal tension to be generated by each belt and full or primary tension to be applied substantially over the entire width of the lower back support member; and accordingly, the lower spinal column is more fully protected when heavy exercises are being performed. Not only is full tension provided over a wide area of the back, but the weightlifter's comfort level is greatly enhanced by the selective adjustment made to any one of the dual belts.

The dual component belt configuration of this invention also allows the weightlifter to revert from applying full back tension to a reduced tension, and this is normally done when there is a switch in performing heavy to light exercises. It is the usual weightlifter's practice mode to begin his exercise with heavy moves and then close by engaging in several light moves.

Another benefit resulting from the present invention resides in the minimization of stretch that occurs over the prior art single belt due to a sharing of the tension that is developed between the dual belts when they are tightened against the body of the weightlifter.

It is therefore an object of the invention to provide a new and improved waist support member.

It is still another object of the invention to provide a new and improved weightlifting support member that supplies uniform tension in the abdomen and lower back areas during the execution of heavy exercises.

It is a further object of the invention to furnish a new and improved weightlifting support member that can be readily modified for either heavy or light exercise moves.

BRIEF DESCRIPTION OF THE DRAWINGS

FIG. 1 depicts an isometric view of the weightlifter's double belt configuration of the present invention.

FIG. 2 further depicts the shape as viewed from the rear of a belt blank which is utilized to configure the double belt of FIG. 1.

FIG. 3 illustrates a cross sectional view 3—3 taken through the lower portion of FIG. 1.

DESCRIPTION OF THE PREFERRED EMBODIMENT

Referring in detail to the isometric drawing of FIG. 1, there is shown the weightlifter's training belt 10 of the present invention which is comprised of component belts 7, 8 for providing support to abdomen and lower back skeletal and muscle areas during the performance of exercise programs. The dual belts 7, 8 are initially fabricated by forming lower and upper tongue members 12a, 14a which are integrally joined to and extend from one end of an oblong shaped member 16 as seen in FIG. 2; and, lower and upper attaching members 12b, 14b, which are substantially identical to members 12a, 14a are made to integrally extend from an opposite end of the oblong member 16. In the preferred embodiment, the belt is fabricated from fourteen ounce leather which is durable as well as easily flexible and provides strong support when placed in position around the weightlifter's waist during various weightlifting exercises. A top to bottom height dimension of the oblong member 16 is five and one-half inches, whereas, a top to bottom dimension of lower tongue member 12a to upper tongue member 14a and lower attaching member 12b to upper attaching member 14b is four and one-half inches; and, these dimensions are to be contrasted with a single belt Olympic style configuration (not shown), which has a height dimension around its entire circumference of four inches with a thickness of three-eighths of an inch. However, it has been estimated that the Olympic style belt, which is used for competition purposes, is three times more expensive than the belt of the present invention. In the tongue members 12a, 14a there are formed a plurality of equally spaced holes wherein the holes in belt 7 are off-set with respect to the holes in belt 8 in a staggered orientation. The staggered holes 18, 20, 22, for example, are arranged in a configuration wherein the same numbered hole in tongue member 14a is one-half space unit behind an identically numbered hole in tongue member 12a; as for example, the sixth hole 22 from the end in tongue member 14a is one-half unit being the sixth hole 20 in member 12a. A plurality of holes are also provided in the attaching member 12b wherein bracketed holes x are formed as a mirror image of bracketed holes y; and similarly, bracketed holes p formed in attaching member 14b are made into a mirror image of bracketed holes q. However, the bracketed holes x, y are formed in a different pattern from the bracketed holes p, q as discussed hereinafter. The set of bracketed holes x, y, for example, are adapted to receive fastener rivets 17, 19, 21 for holding a buckle 13 and loop 23 (see FIG. 3) permanently in position upon a folding of attaching member 12b back upon itself in a manner to align bracketed holes x with bracketed holes y. Slot formations 30, 32 are also provided in respective attaching members 12b, 14b between the bracketed set of mirrored holes x, y and the bracketed set of mirrored holes p, q. A fuller description of the utility of the slot formations 30, 32 as well as for the different pattern of the bracketed holes x, y from holes p, q, and the significance of the staggered hole formation in tongue members 12a, 14a will be set forth in later paragraphs.

The sectional view of FIG. 3 depicts how the buckle 13 and loop 23 are firmly retained as component parts of the belt 7 by strategic positioning upon attaching member 12b. Initially this is carried out by threading the attaching member 12b through a rectangular frame (not shown) of the buckle 13 such that the male member 13a, which swivels upon buckle post 13b, is allowed to be placed through the slot 30. Upon threading through the buckle frame and positioning the male member 13a through the slot 30 the attaching member 12b is folded back around post 13b so that the bracketed holes x become aligned with the bracketed holes y (see FIG. 2). The alignment of the bracket holes x and y when attaching member 12b is folded back upon itself also causes the dotted columnar sections to coincide with one another. With the alignment of the bracketed holes x and y upon the folding back upon itself of attaching member 12b, a rivet 17 is fixed in place in order to permanently attach the buckle 13 to the post 13b and in particular to belt 7. The loop or retainer 23 (see FIG. 1) is positioned on the belt 7 by locating its rearwardly facing section 23b between the folded back attaching member 12b and in the space provided by the coinciding columnar sections. The rivets 19, 21 are utilized for fixing the loop 23 in place upon member 12b. A freely rotatable roller 13e is located around a vertical post 13d of buckle 13 to facilitate the semi-permanent attachment of the tongue 12a with the buckle 13 by locating the male member 13a through one of the staggered holes 18, 20 when circumferentially surrounding the waist of the weightlifter. The structural configuration and the connection of the buckle 15 to the attaching member 14b to allow for the semi-permanent connection with the tongue member 14a is identical to the connection of the buckle 13 with the tongue member 12a as previously described.

However, the positioning of the loop 25 upon attaching member 14b is off-set with respect to the positioning of loop 23 upon attaching member 12b in order to eliminate interference with one another and to prevent excessive separation of the belts 7, 8. It has been found that when the loops 23, 25 come together and create interference the belts 7, 8 separate from one another rather than remaining juxtaposed; and, the effect is that a gap is created in a manner that will cause the weightlifter's skin to be pinched as it enters the created separation. In order to provide the off-set positioning between loops 23, 25 a rearwardly facing section 25b (see FIG. 1) is located within a space designated by the dotted columnar sections (see FIG. 2), which are made to coincide when the attaching member 14b is folded back upon itself after passing firstly around a vertical post (not shown) of buckle 15. By this arrangement the loop 25 is positioned so that it is oriented a greater distance from buckle 15 than is the loop 23 from buckle 13 in order to prevent the above-mentioned interference and excessive gap formation. Nevertheless, off-set interference would occur if loop 25 were positioned ahead of loop 23 and the two belts 7, 8 were tightened to create equal support tension in the waist area due to some minimum stretching that is created in upper belt 8. Even though there is a one-half space differential caused by staggering of the holes in order to allow the equal support tensions to be developed in each belt 7, 8, a stretching occurs in upper belt 8 due to the shape of the human torso when ascending from the smallest circumference in the waist area and surrounded by belt 7 to the larger dimension created by a contiguous circumference surrounded by belt 8. This stretching of belt 8 tends to cause the loop 25 to move counterclockwise as viewed in FIG. 1 and would create interference by impinging upon loop 23. No interference and no gap is created by the orientation in accordance with the present invention as depicted in FIG. 1 since the loop 25 is positioned beyond loop 23 and its tendency to move counterclockwise due to stretching is without consequence.

When the weightlifter who is engaged in practicing the principles of the present invention is ready to perform heavy exercises such as heavy squats or overhead presses for developing upper body strength and muscalature, the oblong shaped member 16 is located over the lumbar vertebrae region and the lower half of the dorsal region of the lower back including a broad flat muscle known as the latissimus dorsi. A muscle referred to as the erector spinae, a deeper muscle in the lower back area than the dorsi and located on either side of the spine, is also covered by the oblong member 16. As the oblong shaped member 16 is brought around to the side of the waist it provides support to a muscle known as the descending oblique, which is situated on the side and fore part of the abdomen. The tongue members 12a, 14a when semi-permanently attached to the buckles 13, 15 are positioned around the waist to provide support in the vicinity of the umbilicus and over the rectus abdominus, which is a long flat muscle which extends along the whole length of the front of the abdomen. The weightlifter who is performing heavy exercises such as presses while stretched upon a bench incurs severe arching of the back and a bulging of the abdomen caused by trying to gain leverage through the chest. The arching of the back that occurs during this type of exercise places the lumbar and dorsal vertebrae of the lower back in compression whereas the abdominal muscles are expanded. Severe arching of the back also places the spinal column in the lumbar area with its various vertebrae together with the covering muscle complex above mentioned in an undesirably exaggerated position, which creates dangerous pressure on the spinal discs, adjoining vertebrae and muscalature. The simultaneous expansion and compression may cause the pinching of the intervertebral discs which potentially can develop into a herniated condition.

The dual belt arrangement 10 of this invention when positioned around the waist in accordance with the individual tightening of each tongue member 12a, 14a minimizes compression and expansion in the respective back and abdomen areas to prevent injury. Furthermore, the belt 10 widens the application of primary tension applied to the arched back of the weightlifter over the single belt configuration of the known prior art. This improvement may be viewed by referring to FIG. 1 wherein traverse force lines 40 developed by the instant invention are depicted as applying primary tension across the entire oblong shaped member 16. In contrast, the prior art single belt develops both primary and secondary tension across the oblong shaped member 16 where the primary tension is identified by the vertical force lines 41 and the secondary tension by oblique force lines 42, 43. As a consequence of the primary tension applied across the entire width dimension of the oblong member 16 more of the lumbar and dorsal vertebrae as well as the erector, oblique and dorsi muscles are supported when the back is being severely arched; in contrast, the single belt does not supply primary tension to the extremities of the belt as indicated by the secondary tension and as represented by the secondary force lines 42, 43. Hence, the support provided to the arched back is only minimally favorable to the weightlifter.

The dual belt 10 of the instant invention provides substantially improved comfort to the wearer over the single belt prior art configuration since it allows equal tension to be developed by each belt 7, 8, while making an accommodation of the varying circumferential dimensions of the weightlifter's torso with the staggered hole arrangement. This feature is significant because the added comfort level that is created enhances the pleasure that is generated in a weight training program. In view of the vigorous body movements required by participants in such a program the elimination of any discomfiture that might be created is of much benefit.

Another significant advantage of the present staggered hole, off-set loop exercise belt 10 resides in the longer useful life that is developed over the prior art single belt. This longer life is achieved by minimal stretch being developed in the material in using two component belts 7, 8, since the tension that is achieved by the belt 10 when tightened against the waist is shared rather than completely carried as by the single belt arrangement. When the single belt material is stretched the original holes when coupled to a male buckle member do not provide the same tension to the lumbar and abdomen areas as originally designed, and therefore the hole structure must be modified after a time to produce the original support tension. The forming of modified holes in the belt in order to provide its original tension is a serious shortcoming of the prior art.

The above description of the dual belt arrangement of the weightlifting training belt 10 has been related to heavy exercise programs. The training belt 10 however is easily adaptable when the weightlifter reverts to light exercises such as arm curls, and in this case, full support tension is obviously not required. However, to provide some support tension to the lower back and abdomen regions when performing light exercises, the weightlifter may modify the training belt 10 by disconnecting the upper component belt 8 (see FIG. 1) and allowing the lower component belt 7 to remain in place around the waist circumference. The versatility of the belt 10 is easily recognized since it is readily adaptable for use in either heavy or light exercises.

This invention has been described by reference to precise embodiments but it will be appreciated by those skilled in the art that this invention is subject to various modifications and to the extent that those modifications would be obvious to one of ordinary skill they are considered as being within the scope of the appended claims.

What is claimed is:

1. A belt arrangement for use in the practice of weightlifting comprising:
   (a) a flexible member which is integrally formed to provide first and second contiguous belts which respectively include tongue and buckle members, said first belt being utilized with respect to the narrowest dimension of the waist;
   (b) a plurality of holes formed in said respective first and second belts wherein the holes in the first belt are staggered with respect to the holes in the second belt for allowing each to develop equal tension in the waist area with respect to one another and full tension across the lumbar region when said respective buckles and tongues are tightened around the weightlifter's waist;
   (c) first and second loop members wherein a respective first loop is attached to said first belt and said second loop is attached to said second belt, and wherein said first loop is positioned closer to the buckle associated with the first belt than is the buckle associated with the second belt to prevent interference with one another and to prevent a gap from being formed between the belts.

2. A belt arrangement for use in the practice of weightlifting comprising:
   (a) a flexible and oblong shaped member for positioning against an extended lower back area of a weightlifter during an exercise program;
   (b) first and second tongue members extending from one end of said oblong shaped member, and each tongue member being of equal length and including a plurality of holes wherein said holes of said first and second tongue member are alternately spaced with respect to one another in a staggered manner;
   (c) first and second attaching members extending from a second end of said oblong shaped member and said first attaching member including first and second plurality of holes which are mirror images of one another, and said second attaching member including third and fourth plurality of holes which are mirror images of one another and wherein the plurality of mirrored holes of said first attaching member being different from the plurality of mirrored holes of said second attaching member;
   (d) first and second buckle means, and said respective first and second attaching members being adapted for passing through said buckle means and folding back upon themselves to bring said mirrored holes into alignment;
   (e) means placed into said aligned holes for fixing said respective first and second buckles to said respective first and second attaching members;
   (f) said first attaching member and buckle means being semi-permanently attached to said first tongue member through one of said staggered holes as a first belt for surrounding a narrowest waist dimension of said weightlifter;

(g) said second attaching member and buckle being semi-permanently attached to said second tongue member through one of said plurality of alternately spaced holes as a second belt for surrounding the waist having a larger waist dimension but contiguous to said first waist dimension;

(h) a tightening of said first belt against said narrowest waist dimension providing a first level of support to the lower back and abdomen areas of said weightlifter, and a tightening of said second belt against said second larger waist dimension providing an equivalent level of support to said contiguous area of the lower back and abdomen areas in order to provide substantially equal tension across the entire oblong shaped member when positioned against the weightlifter's back area while conducting heavy exercise moves.

3. The belt arrangement in accordance with claim 2 wherein said second belt may be adjusted to provide nonsupport with respect to the first level support provided by said first belt, and said first support level being utilized only for conducting light weightlifting moves.

4. A belt arrangement in accordance with claim 2 and further including first and second loops respectively positioned between said folded back first and second attaching means and in a location as determined by said different plurality of mirrored holes wherein said first loop is positioned at a distance closer to said first buckle than the distance between said second loop with respect to said second buckle.

5. A belt arrangement in accordance with claim 2 wherein said oblong shaped member and said first and second tongue and attaching members are integrally formed.

* * * * *